United States Patent [19]

Kamiya et al.

[11] 4,010,178

[45] Mar. 1, 1977

[54] CARBONIC ACID ESTERS, AND THE PREPARATION THEREOF AND THEIR USE

[75] Inventors: Takashi Kamiya, Suita; Masumi Itoh, Takatsuki; Daijiro Hagiwara, Ikeda, all of Japan

[73] Assignee: Fujisawa Pharmaceutical Co., Ltd., Osaka, Japan

[22] Filed: Aug. 26, 1975

[21] Appl. No.: 607,759

[30] Foreign Application Priority Data

Aug. 27, 1974 Japan ............................... 49-98702
Sept. 21, 1974 Japan ............................ 49-109362
Oct. 10, 1974 Japan ............................ 49-115856

[52] U.S. Cl. ........................... 260/308 B; 260/463
[51] Int. Cl.² ........................................ C07D 249/18
[58] Field of Search ...................... 260/308 B, 463

[56] References Cited

UNITED STATES PATENTS 3,189,615  6/1965  Heller et al. ...................... 260/308

*Primary Examiner*—Lewis Gotts
*Assistant Examiner*—Cary Owens
*Attorney, Agent, or Firm*—Bierman & Bierman

[57] ABSTRACT

Carbonic acid esters of the formula substituent(s) substituents(s)

$$R'_1OCOOR'_2$$

wherein $R'_1$ is lower alkyl which may have substituent(s)) selected from the group of halogen, lower alkoxy and aryloxy, or ar(lower)-alkyl which may have substituents)s) selected from the group of lower alkoxy, halogen, nitro and cyano, and $R'_2$ is benzotriazolyl which may have halogen; or a group represented by the formula:

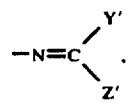

wherein Y' and Z' are each cyano, nitro, carbamoyl, esterified carboxy, lower alkanoyl, aroyl or disubstituted carbamoyl; provided that when $R'_2$ is a group represented by the formula:

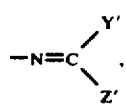

wherein Y' and Z' are each cyano, nitro, carbamoyl or esterified carboxy, $R'_1$ is ar(lower) alkyl having substituent(s) selected from the group of lower alkoxy, halogen, nitro and cyano.

A process for the protection of amino and/or imino groups in compounds containing them by reacting them with the aforementioned esters is also disclosed.

22 Claims, No Drawings

CARBONIC ACID ESTERS, AND THE PREPARATION THEREOF AND THEIR USE

The present invention relates to new carbonic acid ester which is useful as an agent for introducing esterified carboxy-type protective group(s) on amino and/or imino group(s) in amino and/or imino group(s)-containing compounds and to processes for the preparation thereof.

Further, the present invention relates to a process for the temporary protection of amino and/or imino group(s) in amino and/or imino group(s)-containing compounds with esterified carboxy-type protective group(s).

As is known, such a temporary protection of amino and/or imino group(s) is of great importance in the field of preparative chemistry as well as of degradation reactions, for example, in peptide-chemistry, penicillin-chemistry, cephalosporin-chemistry, alkaloid-chemistry, determination of the constitution of unknown compounds such as natural products, and the like.

The present invention is based on the observation that a carbonic acid ester of the formula (I) as shown below is a much more favorable agent for the temporary protection of amino and/or imino group(s) in the compound in comparison with the agents which have been conventionally employed in the arts in the following regards. That is to say:

1. that said carbonic acid ester is present in stable oil or crystals and is free from explosiveness, corrosiveness or irritativeness which are often caused by the conventional agents so that it is much more favourable and safe for handling in experimentally as well as industrially practical use,
2. that said carbonic acid ester can be easily prepared, and
3. that said carbonic acid ester reacts rather rapidly with amino and/or imino group(s)-containing organic compounds under milder reaction conditions to give protected amino and/or imino group(s)-containing compound so that undesired troublesome side reactions and production of by-products, which often occur unfavourably in case of using the conventional agents, can be minimized or in some case substantially avoided. And, in such a reaction of said carbonic acid ester with the amino and/or imino group(s)-containing compound, there may be produced a compound of the formula:

wherein $R_2$ is as defind below, as a substantially sole by-product, which can be so easily recovered in pactical purity from the reaction mixture by a conventional manner such as extraction and may be used repeatedly without any further purification, as a starting material, for the preparation of the compound (I) of the present invention.

Accordingly, the present invention provides a process for the protection of amino and/or imino group(s) in an amino and/or imino group(s)-containing compound, which comprises reacting an amino and/or imino group(s)-containing compound with a carbonic acid ester of the formula:

 (I)

wherein $R_1$ is lower alkyl which may have substituent(s) selected from the group of halogen, lower alkoxy and aryloxy, or ar(lower)alkyl which may have substituent(s) selected from the group of lower alkoxy, halogen, nitro and cyano, and $R_2$ is benzotriazolyl which may have halogen; or a group represented by the formula:

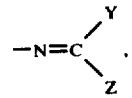

wherein Y and Z are each aryl which may have substituent(s) selected from the group of halogen, lower alkoxy, nitro, cyano and halo(lower)alkyl, or an electron withdrawing group.

According to said reaction, the esterified carboxy group ($R_1OCO-$) in the carbonic acid ester (I) can be introduced on the amino and/or imino group(s) in the amino and/or imino group(s)-containing compound for the protection to provide the protected amino and/or imino group(s)-containing compound.

For this purpose, there may be used as starting material any desired amino and/or imino group(s)-containing compounds, especially an organic compound including all of an aliphatic, an aromatic or a heterocyclic compound, etc., each of which contains at least one amino or imino group in the molecule.

In this specification and claims, the term "lower" is intended to mean a group having 1 to 6 carbon atom(s) unless otherwise indicated.

A suitable example of lower alkyl for $R_1$ may include one, which may be branched or cyclic and, having 1 to 6 carbon atom(s) such as methyl, ethyl, propyl, isopropyl, butyl, isobutyl, tert-butyl, pentyl, neopentyl, tert-pentyl, hexyl, 1-cyclopropylethyl, cyclopropyl, cyclopentyl, cyclohexyl or the like, and preferably one having 2 to 5 carbon atoms, and these lower alkyl groups may have optionally at least one substituent selected from the group of halogen (e.g., chlorine, bromine, fluorine or iodine), lower alkoxy having 1 to 6 carbon atom(s) (e.g., methoxy, ethoxy, propoxy, isopropoxy, butoxy, tert-butoxy, pentyloxy, hexyloxy, etc.) and aryloxy having 6 to 10 carbon atoms (e.g., phenoxy, tolyloxy, xylyloxy, naphthloxy, etc.).

A suitable example of ar(lower)alkyl for $R_1$ may include one having 7 to 10 carbon atoms such as benzyl, phenethyl, tolylmethyl, xylylmethyl, mesitylmethyl or the like, and preferably one having 7 to 8 carbon atoms, and these ar(lower)alkyl groups may have optionally at least one substituent selected from the group of the aforementioned lower alkoxy, halogen, nitro and cyano.

A suitable example of aryl for Y and Z may include one having 6 to 10 carbon atoms such as phenyl, tolyl, xylyl, mesityl, cumenyl, naphthyl or the like, and these aryl groups may have optionally at least one substituent selected from the group of the aforementioned halogen, lower alkoxy, nitro, cyano and halo (lower)alkyl (e.g., trichloromethyl, trifluoromethyl, etc.).

A suitable electron withdrawing group for Y and Z may include cyano; nitro; an acyl such as lower alkanoyl having 1 to 6 carbon atom(s) (e.g., formyl, acetyl, propionyl, butyryl, isobutyryl, valeryl, isovaleryl, pivaloyl, etc.), aroyl having 7 to 11 carbon atoms (e.g., benzoyl, toluoyl, xyloyl, naphthoyl, etc.), esterified carboxy, for exmple, lower alkoxycarbonyl having 2 to 7 carbon atoms (e.g., methoxycarbonyl, ethoxycarbonyl, propoxycarbonyl, isopropoxycarbonyl, butoxycarbonyl, isobutoxycarbonyl, tert-butoxycarbonyl, 1-cyclopropylethoxycarbonyl, cyclohexyloxycarbonyl, etc.), ar(lower)alkoxycarbonyl having 8 to 9 carbon atoms (e.g., benzyloxycarbonyl, phenethyloxycarbonyl, etc.) or aryloxycarbonyl having 7 to 8 carbon atoms (e.g., phenoxycarbonyl, tolyoxycarbonyl, etc.), carbamoyl, disubstituted carbamoyl, for example, di(-lower)alkylcarbamoyl (e.g., dimethylcarbamoyl, diethylcarbamoyl, methylethylcarbamoyl, dipropylcarbamoyl, diisopropylcarbamoyl, dibutylcarbamoyl, etc.), lower alkylarylcarbamoyl (e.g., methylphenylcarbamoyl, ethylphenylcarbamoyl, etc.) or diarylcarbamoyl (e.g., diphenylcarbamoyl, ditolylcarbamoyl, etc.) or the like; or the like.

A suitable example of benzotriazolyl for $R_2$ may include 1H-benzotriazolyl or 2H-benzotriazolyl, and these groups may have at least one of the aforementioned halogen.

The present reaction may be conducted in a conventional manner, i.e. under conditions which have been used in the known reaction for the protection of amino and/or imino group(s) in the compound with an esterified carboxy group. More particularly, the reaction may be conducted in a conventional solvent such as water, an alcohol (e.g., methanol, ethanol, propyl alcohol, butyl alcohol, tert-butyl alcohol, etc.), ethyl acetate, chloroform, dimethylformamide, methylene chloride, tetrahydrofuran, acetone or the like, or a mixture thereof, or other solvents which do not adversely affect the present reaction. The reaction may be optionally carried out in the presence of a base such as an inorganic base, for example, an alkali metal hydroxide (e.g., sodium hydroxide, potassium hydroxide, etc.), an alkaline earth metal hydroxide (e.g., calcium hydroxide, magnesium hydroxide, etc.), an alkali metal carbonate (e.g., sodium carbonate, potassium carbonate, etc.), an alkaline earth metal carbonate (e.g., calcium carbonate, magnesium carbonate, etc.), an alkali metal bicarbonate (e.g., sodium bicarbonate, potassium bicarbonate, etc.), or the like; an organic base, for example, an alkali metal acetate (e.g., sodium acetate, potassium acetate, etc.), trialkylamine (e.g., trimethylamine, triethylamine, etc.), triethanolamine, N,N-dimethylaniline, N,N-dimethylbenzylamine, N,N'-dimethylpiperazine, N-methylmorpholine, pyridine, quinoline, or the like; or a basic ion-exchange resin, or a mixture thereof.

The reaction temperature is not particularly limited, but the reaction is preferably carried out around room temperature.

The product having the protected amino and/or imino group(s) thus prepared can be isolated by a conventional method.

Thus prepared the protected amino and/or imino group(s)-containing compound can be used for further synthesis of known or new compounds, in which it is inevitable to protect amino and/or imino group(s) in the compound in order to avoid any side-reaction, production of by-product and the like. And, the protected amino and/or imino group(s)-containing product thus synthesized may be subsequently subjected to scission of the said protective group, i.e., esterified carboxy group, to regenerate the free amino and/or imino group(s)-containing product. Such subsequent scission of the esterified carboxy type protective group(s) can be carried out by a conventional method.

The representative examples of the present carbonic acid ester (I) may be illustrated as follows:

2-Lower alkoxycarbonyloxyimino-2-cyanoacetamide (e.g., 2-ethoxycarbonyloxyimino-2-cyanoacetamide, 2-isobutoxycarbonyloxyimino-2-cyanoacetamide or 2-methoxycarbonyloxyimino-2-cyanoacetamide), di(-lower)alkyl 2-lower alkoxycarbonyloxyiminomalonate (e.g., diethyl 2-ethoxycarbonyloxyiminomalonate or diethyl 2-tert-butoxycarbonyloxyiminomalonate), lower alkyl 2-lower alkoxycarbonyloxyimino-2-cyanoacetate (e.g., ethyl 2-ethoxycarbonyloxyimino-2-cyanoacetate, ethyl 2-isobutoxycarbonyloxyimino-2-cyanoacetate, ethyl 2-methoxycarbonyloxyimino-2-cyanoacetate or ethyl 2-tert-pentyloxycarbonyloxyimino-2-cyanoacetate), lower alkyl 2-halo(lower)alkoxycarbonyloxyimino-2-cyanoacetate [e.g., ethyl 2-(2,2,2-trichloroethoxycarbonyloxyimino)-2-cyanoacetate], lower alkyl 2-ar(lower)alkoxycarbonyloxyimino-2-cyanoacetate (e.g., ethyl 2-benzyloxycarbonyloxyimino-2-cyanoacetate), lower alkyl 2-lower alkoxycarbonyloxyiminoacetoacetate (e.g., ethyl 2-tert-butoxycarbonyloxyiminoacetoacetate), di(lower)alkyl 2-lower alkoxy substituted ar(lower)alkoxycarbonyloxyiminomalonate [e.g., diethyl 2-(4-methoxybenzyloxycarbonyloxyimino)malonate], 2-lower alkoxycarbonyloxyimino-1-aryl(lower)alkane-1,3-dione (e.g., 2-tert-butoxycarbonyloxyimino-1-phenylbutane-1,3-dione), 1-lower alkoxycarbonyloxy-6-halobenzotriazole (e.g., 1-tertbutoxycarbonyloxy-6-chloro-1H-benzotriazole or 1-ethoxycarbonyloxy-6-chloro-1H-benzotriazole), 1-ar(lower) alkoxycarbonyloxybenzotriazole (e.g., 1-benzyloxycarbonyloxy-1H-benzotriazole), 2-lower alkoxycarbonyloxyimino-2-arylacetonitrile [e.g., 2-tert-butoxycarbonyloxyimino-2-phenyl-acetonitrile, 2-tert-butoxycarbonyloxyimino-2-(1-naphthyl) acetonitrile or 2-(1-cyclopropylethoxycarbonyloxyimino)-2-phenylacetonitrile], benzophenone O-lower alkoxycarbonyloxime (e.g., benzophenone O-tert-butoxycarbonyloxime), 2-halo(lower)alkoxycarbonyloxyimino-2-arylacetonitrile [e.g., 2-(2,2,2-trichloroethoxycarbonyloxyimino)-2-phenylacetonitrile], 2-lower alkoxy substituted or unsubstituted ar(lower)alkoxy-carbonyloxyimino-2-arylacetonitrile [e.g., 2-(4-methoxybenzyloxycarbonyloxyimino)-2-phenylacetonitrile or 2-benzyloxycarbonyloxyimino-2-phenylacetonitrile], 2-lower alkoxycarbonyloxyimino-2-halogen substituted arylacetonitrile [e.g., 2-tert-butoxycarbonyloxyimino-2-(4-chlorophenyl)acetonitrile] or the like.

The carbonic acid ester of the formula (I) to be used for the said protection includes new and known compounds, and the present invention also provides new carbonic acid esters and processes for the preparation thereof.

The new carbonic acid ester is represented by the following formula:

 (I')

wherein $R'_1$ is lower alkyl which may have substituent(s) selected from the group of halogen, lower alkoxy and aryloxy, or ar(lower)alkyl which may have substituent(s) selected from the group of lower alkoxy, halogen, nitro and cyano, and $R'_2$ is benzotriazolyl which may have halogen; or a group represented by the formula:

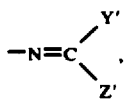

wherein Y' and Z' are each aryl which may have substituent(s) selected from the group of halogen, lower alkoxy, nitro, cyano and halo(lower)alkyl, cyano, nitro, carbamoyl, esterified carboxy, lower alkanoyl, aroyl or disubstituted carbamoyl; provided that when $R'_2$ is a group represented by the formula:

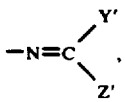

wherein Y' and Z' are each cyano, nitro, carbamoyl or esterified carboxy, $R'_1$ is ar(lower)alkyl having substituent(s) selected from the group of lower alkoxy, halogen, nitro and cyano;

and further provided that when $R'_1$ is lower alkyl and $R'_2$ is a group represented by the formula:

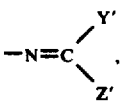

wherein Y' is cyano and Z' is aryl, the number of carbon atoms of lower alkyl for $R'_1$ is 4 or 5.

Suitable examples of lower alkyl and ar(lower)alkyl for $R'_1$ and the substituents thereof may be the same ones as illustrated as the examples of the definitions for $R_1$, respectively.

Suitable examples of aryl, the substituents thereof, esterified carboxy, lower alkanoyl, aroyl and disubstituted carbamoyl for Y' and Z' may be the same ones as illustrated as the examples of the definitions for Y and Z, and the suitable examples of benzotriazolyl and the substituent thereof for $R'_2$ may be the same ones as illustrated as the examples of the definitions for $R_2$, respectively.

The new carbonic acid ester of the formula (I') can be prepared by reacting a haloformic acid ester of the formula:

X—COOR'$_2$  (II)

wherein X is halogen and $R'_2$ is as defined above, with a hydroxy-compound of the formula:

$R'_1$ — OH  (III)

wherein $R'_1$ is as defined above.

A suitable example of halogen for X can be also referred to the ones exemplified as the substituent of lower alkyl for $R_1$.

The reaction of the compound (II) with the compound (III) is usually carried out in a conventional solvent such as chloroform, tetrahydrofuran, ether, acetonitrile, ethyl acetate, acetone, benzene, n-hexane, petroleum ether, dioxane or any other organic solvent which does not adversely affect the reaction. These solvents may also be used in a mixture thereof. The reaction is preferably carried out in the presence of a base such as inorganic base, for example, alkali metal hydroxide (e.g., sodium hydroxide, potassium hydroxide, etc.), alkaline earth metal hydroxide (e.g., calcium hydroxide, magnesium hydroxide, etc.), alkali metal carbonate (e.g., sodium carbonate, potassium carbonate, etc.), alkaline earth metal carbonate (e.g., calcium carbonate, magnesium carbonate, etc.), alkali metal bicarbonate (e.g., sodium bicarbonate, potassium bicarbonate, etc.) or the like, or organic base (e.g., trimethylamine, triethylamine, triethanolamine, dimethylaniline, pyridine, quinoline, etc.). These bases may be used alone or in combination. The reaction temperature is not limitative, and the reaction is preferably carried out around room temperature or comparatively lower temperature.

Alternatively, the new carbonic acid ester (I') can be prepared by reacting a formic acid ester of the formula:

$R'_1$ — OCOX'  (IV)

wherein $R'_1$ is as defined above and X' is halogen, with a compound of the formula:

$R'_2$ — OH  (V)

wherein $R'_2$ is as defined above or a salt thereof.

The suitable halogen for X' is also referred to the ones exemplified as the substituent of lower alkyl for $R_1$.

The suitable salt of the compound (V) is also referred to the ones exemplified below for the compound (VI).

In the present reaction, there can be employed almost the same solvent, base and reaction temperature as those employed in the reaction of the compound (II) with the compound (III) as mentioned above, and in addition, water or its mixture with the solvents mentioned above may also be used optionally according to the property of the compound (IV).

The compound (I') can be also prepared by reacting a mixture of the compounds (V) or a salt thereof, (III) and (VII) or a reactive equivalent thereof, in which the reaction may proceed via the same mechanism of reacting the compound (II) with the compound (III) and/or reacting the compound (IV) with the compound (V).

The starting compound (II) to be used in the above process include partially new compounds, which are represented by the following formula:

X — COOR''$_2$  (II')

wherein X is as defined above and $R''_2$ is benzotriazolyl which may have halogen; or a group represented by the formula:

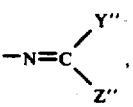

wherein

Y" is aryl which may have substituent(s) selected from the group of halogen, lower alkoxy, nitro, cyano and halo(lower)alkyl, cyano, nitro, carbamoyl, esterified carboxy, lower alkanoyl, aroyl, or disubstituted carbamoyl and Z" is naphthyl, aryl having substituent(s) selected from the group of halogen, lower alkoxy, nitro, cyano and halo(lower)alkyl, lower alkanoyl, aroyl or disubstituted carbamoyl.

The said new starting compounds (II') can be prepared by reacting a compound of the formula:

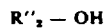  (VI)

wherein

R"$_2$ is as defined above, or a salt thereof with a carbonyl halide of the formula:

  (VII)

wherein X is as defined above, or a reactive equivalent thereof.

A suitable salt of the compound (VI) may include alkali metal salt (e.g., sodium salt, potassium salt, etc.), alkaline earth metal salt (e.g., calcium salt, magnesium salt, etc.) or the like.

A suitable reactive equivalent of the compound (VII) may include polymer of the compound (VII), for example, the dimer (trichloromethyl chloroformate) or trimer [di(trichloromethyl) carbonate] of the compound (VII), in which the suitable halogen for X is chlorine.

The reaction of the compound (VI) with the compound (VII) is usually carried out in a conventional solvent such as benzene, toluene, tetrahydrofuran, dioxane or any other organic solvent which does not adversely affect the reaction. The solvent may be used alone or in combination. The reaction is preferably carried out in the presence of a base such as inorganic base for example, alkali metal hydroxide (e.g., sodium hydroxide, potassium hydroxide, etc.), alkaline earth metal hydroxide (e.g., calcium hydroxide, magnesium hydroxide, etc.), alkali metal carbonate (e.g., sodium carbonate, potassium carbonate, etc.), alkaline earth metal carbonate (e.g., calcium carbonate, magnesium carbonate, etc.), alkali metal bicarbonate (e.g., sodium bicarbonate, potassium bicarbonate, etc.) or the like, or organic base (e.g., triethylamine, pyridine, dimethylaniline, etc.). The reaction temperature is not limitative, and the reaction is preferably carried out under cooling or around room temperature.

In this process, the compound (II'), may be isolated from the reaction mixture, and also the reaction mixture per se can be preferably employed for the successive reaction with the compound (III) without isolating the compound (II').

Among the carbonic acid ester of the formula (I) and the haloformic acid ester of the formula (II), known compound also can be prepared according to substantially the same method as mentioned in the explanation of the processes for preparing the new carbonic acid ester (I') and the new haloformic acid ester of the formula (II'), respectively.

The following examples are given for the purpose of illustrating the present invention:

EXAMPLE 1

Process for the protection of amino and/or imino group(s)

A. Triethylamine (0.42 ml.) was added to a suspension of D-2-(3-mesylaminophenyl)glycine (488 mg.) and diethyl 2-tertbutoxycarbonyloxyiminomalonate (770 mg.) in a mixture of tert-butyl alcohol (10 ml.) and water (10 ml.), and the mixture was stirred for 1.5 hours at room temperature. To the reaction mixture were added water and a sodium bicarbonate aqueous solution, and then ethyl acetate, after which the mixture was adjusted to pH 7 with a citric acid aqueous solution. The aqueous layer was separated, washed with ethyl acetate, adjusted to pH 3.5 with a citric acid aqueous solution and extracted with ethyl acetate. The extract was washed with water, dried over magnesium sulfate and concentrated to give N-tert-butoxycarbonyl-D-2-(3-mesylaminophenyl)glycine (634 mg.).
$[\alpha]_D = -96°$ (methanol, C=1)
Nuclear Magnetic Resonance Spectrum [(CD$_3$)$_2$SO, $\delta$]; ppm 7.00 - 7.60 (5H, m); 5.11 (1H, d, J=8Hz); 3.00 (3H, s); 1.40 (9H, s).

B. D-2-(3-Mesylaminophenyl)glycine (2.44 g.) was suspended in a mixture of methanol: water (1:1) (volume ratio) (25 ml.) and dissolved by adding triethylamine (2.1 ml.). To the solution was dropwise added a solution of diethyl 2-tert-butoxycarbonyloxyiminomalonate (3.47 g.) in methanol (15 ml.) over 10 minutes at 10° to 15° C, and the mixture was stirred for 2 hours at room temperature. The solvent was distilled off under reduced pressure to about ⅓ of the whole volume from the reaction mixture and to the residue were added water (30 ml.) and a saturated sodium bicarbonate aqueous solution (10 ml.). Ethyl acetate (40 ml.) and 0.5N hydrochloric acid (26 ml.) were added to the mixture and then the mixture was shaken. The aqueous layer was separated and ethyl acetate (100 ml.) was added thereto, after which the mixture was adjusted to pH 7.20 with 0.5N hydrochloric acid (12 ml.). The aqueous layer was again separated, adjusted to pH 2.6 with 0.5N hydrochloric acid (27 ml.), followed by addition of a saturated sodium chloride aqueous solution, and extracted twice with ethyl acetate (150 ml.). The extract was washed with a saturated sodium chloride aqueous solution, dried over magnesium sulfate and treated with activated charcoal, and the solvent was distilled off under reduced pressure to give N-tert-butoxycarbonyl-D-2-(3-mesylaminophenyl)glycine (3.50 g.).

C. A solution of diethyl 2-tert-butoxycarbonyloxyiminomalonate (700 mg.) in acetone (5 ml.) was dropwise added to a solution of D-2-(3-mesylaminophenyl)glycine (488 mg.) and triethylamine (0.42 ml.) in a mixture of acetone (5 ml.) and water (5 ml.) over 5 minutes at room temperature, and the mixture was stirred for 2 hours at the same temperature. The reaction mixture was concentrated under reduced pressure and to the residue were added a sodium bicarbonate aqueous solution and water, which brought pH of the solution to 9 to 10. The solution was adjusted to pH 7 with a 0.5M citric acid aqueous solution and washed with ethyl acetate. This aqueous solution was adjusted to pH 3.5 with a 0.5M citric acid aqueous solution and extracted twice with ethyl acetate (30 ml.). The extract was washed with a sodium chloride aqueous solution and dried over magnesium sulfate, and the solvent was distilled off under reduced pressure to give N-tert-butoxycarbonyl-D-2-(3-mesylaminophenyl)glycine (672 mg.), gummy.

D. A solution of diethyl 2-tert-butoxycarbonyloxyiminomalonate (1.9 g.) in tert-butyl alcohol (5 ml.) was added to a solution of L-isoleucine (656 mg.) in a 1N sodium hydroxide aqueous solution (5.0 ml.), and the mixture was stirred for 3 hours at room temperature. tert-Butyl alcohol was removed from the reaction mixture under reduced pressure and water was added to the residue. The mixture was washed with ether, adjusted to pH 3 with a 5% citric acid aqueous solution and extracted with ethyl acetate. The extract was washed with water, dried and concentrated to give N-tert-butoxycarbonyl-L-isoleucine (1.2 g.), oil.

E. Diethyl 2-tert-butoxycarbonyloxyiminomalonate (1.93 g.) was added to a solution of $N^G$-nitro-L-arginine (1.1 g.) and sodium bicarbonate (0.63 g.) in a mixture of water (50 ml.) and tert-butyl alcohol (20 ml.), and the mixture was stirred for 3 hours at room temperature. The reaction mixture was adjusted to pH 7.0 with a citric acid aqueous solution, washed with ethyl acetate, adjusted to pH 3 with a citric acid aqueous solution and extracted with ethyl acetate (100 ml.). The extract was washed with water, dried over magnesium sulfate and concentrated under reduced pressure. The residue was crystallized with a mixture of ethyl acetate and petroleum ether and the precipitates were collected by filtration to give N -tert-butoxycarbonyl-$N^G$-nitro-L-arginine (1.1 g.), mp 114° to 116° C (dec.).

F. L-Phenylalanine (330 mg.) and sodium bicarbonate (202 mg.) were dissolved in water (10 ml.) with heating and allowed to stand. To the solution was added a solution of diethyl 2-(4-methoxybenzyloxycarbonyloxyimino)malonate (1.0 g.) in tert-butyl alcohol (10 ml.) with stirring at room temperature and water (10 ml.) was added thereto, after which the mixture was stirred for 2 hours at room temperature. The reaction mixture was brought to pH 9 by adding water (20 ml.) and a saturated sodium bicarbonate aqueous solution (10 ml.), and water (10 ml.) was added thereto, after which the mixture was washed twice with ethyl acetate (20 ml.). The aqueous layer was adjusted to pH 7 with a 10% citric acid aqueous solution, washed twice with ethyl acetate (30 ml.), adjusted to pH 3.5 with a 10% citric acid aqueous solution and extracted three times with ethyl acetate (30 ml.). The extract was washed with a sodium chloride aqueous solution and dried over magnesium sulfate, and the solvent was distilled off under reduced pressure to give N-(4-methoxybenzyloxycarbonyl)-L-phenylalanine (410 mg.), oil.

G. A solution of ethyl 2-tert-butoxycarbonyloxyiminoacetoacetate (646 mg.) in a mixture of tert-butyl alcohol (5 ml.) and water (5 ml.) was added at once to a solution of L-phenylalanine (330 mg.) and triethylamine (0.28 ml.) in a mixture of tert-butyl alcohol (8 ml.) and water (8 ml.) at room temperature, and the mixture was stirred for 2 hours at room temperature. Water (100 ml.) was added to the reaction mixture and the mixture was adjusted to pH 7 with a 0.5 M citric acid aqueous solution and washed twice with ethyl acetate (40 ml). The aqueous layer was adjusted to pH 3 with a 0.5M citric acid aqueous solution, followed by addition of a sodium chloride aqueous solution, and extracted twice with ethyl acetate (40 ml.). The extract was washed with water and dried, and the solvent was distilled off under reduced pressure to give N-tert-butoxycarbonyl-L-phenylalanine (286 mg.).

H. Triethylamine (1.68 ml.) was added to a suspension of L-alanine (0.89 g.) in a mixture of water (5 ml.) and tert-butyl alcohol (5 ml.) to give homogeneous solution. To the solution was added diethyl 2-tert-butoxycarbonyloxyiminomalonate (4.0 g.) and the mixture was stirred for 1 hour at room temperature. tert-Butyl alcohol was distilled off from the reaction mixture under reduced pressure and to the residue were added ether and a 5% sodium bicarbonate aqueous solution, after which the mixture was adjusted to pH 7 with a citric acid aqueous solution. The aqueous layer was separated and ethyl acetate was added thereto, and the mixture was adjusted to pH 3 with a citric acid aqueous solution. The mixture was shaken enough and the ethyl acetate layer was separated, washed with water and dried. The solution was concentrated under reduced pressure and the residue was recrystallized from a mixture of ether and petroleum ether to give N-tert-butoxycarbonyl-L-alanine (1.59 g.), mp 82° to 84° C.

I. A suspension of 1-tert-butoxycarbonyloxy-6-chloro-1H-benzotriazole (2.7 g.), L-isoleucine (1.3 g) and triethylamine (3.5 ml.) in a mixture of water (8 ml.) and tert-butyl alcohol (12 ml.) was stirred for 2 hours at 60° to 62° C. tert-Butyl alcohol was distilled off from the reaction mixture under reduced pressure and water (15 ml.) was added to the residue. The mixture was adjusted to pH 3 with a citric acid aqueous solution under ice-cooling and extracted with ethyl acetate. The extract was in turn washed with water and a saturated sodium chloride aqueous solution, and then precipitates were filtered off, after which the filtrate was dried over magnesium sulfate. The solution was concentrated and to the residue was added a mixture of ether and petroleum ether (1:1). An insoluble material was filtered off and the filtrate was concentrated under reduced pressure to give N-tert-butoxycarbonyl-L-isoleucine (2.4 g.), oil.

Infrared Absorption Spectrum (Film)
2980, 1725 (shoulder), 1710, 1165 $cm^{-1}$

J. A solution of diethyl 2-tert-butoxycarbonyloxyiminomalonate (4.5 g.) in tert-butyl alcohol (40 ml.) was added at once to a solution of D-2-(3-dimesylaminophenyl)glycine (3.22 g.) and sodium bicarbonate (1.26 g.) in a mixture of tert-butyl alcohol (80 ml.) and water (120 ml.) under ice-cooling and stirring. After stirring for 1.5 hours at room temperature, an insoluble material was filtered off. The filtrate was adjusted to pH 7.5 with a 0.2 M citric acid aqueous solution and tert-butyl alcohol was distilled off under reduced pressure. The residue was washed with ether and adjusted to pH 3 with a 0.2M citric acid aqueous solution. The aqueous solution was saturated with sodium chloride and extracted with ethyl acetate. The extract was washed with a saturated sodium chloride aqueous solution and dried, and the solvent was distilled off under reduced pressure to give N-tert-butoxycarbonyl-D-2-(3-dimesylaminophenyl)-glycine (2.1 g.), foamy solid. Nuclear Magnetic Resonance Spectrum [$(CD_3)_2SO$, δ]; ppm 7.50 (4H, m); 5.20 (1H, d); 3.33 (6H, s); 1.40 (9H, s);

K. N-tert-Butoxycarbonyl-L-phenylalanine was obtained according to a similar manner to that of Example 1 (G) by using L-phenylalanine and 2-tert-butoxycarbonyloxyimino-1-phenylbutane-1,3-dione.

L. N-Benzyloxycarbonyl-L-phenylalanine was obtained according to a similar manner to that of Example 1 (G) by using L-phenylalanine and ethyl 2-benzyloxycarbonyloxyimino-2-cyanoacetate.

M. 6-Benzyloxycarbonylaminopenicillanic acid was obtained according to a similar manner to that of Example 1 (G) by using 6-aminopenicillanic acid and ethyl 2-benzyloxycarbonyloxyimino-2-cyanoacetate.

N. 2-(4-Methoxybenzyl)oxycarbonyloxyimino-2-phenylacetonitrile (1.55 g.) was added to a solution of L-phenylalanine (826 mg.) and triethylamine (0.75 ml.) in a mixture of methanol (10 ml.), dioxane (1.5 ml.) and water (7.5 ml.) at room temperature, and the mixture was stirred for 2 hours at room temperature. The reaction mixture was concentrated, and to the residue were added benzene and a sodium bicarbonate aqueous solution. After shaking the resultant mixture, the aqueous layer was separated from the mixture, washed with ether, acidified with hydrochloric acid and extracted with ethyl acetate. The extract was washed with water, dried and concentrated. To the residue was added n-hexane, and the precipitated crystals were collected by filtration and dried to give N-(4-methoxybenzl)oxycarbonyl-L-phenylalanine (1.064 g.), mp 87°to 88° C.

O. 2-tert-Butoxycarbonyloxyimino-2-phenylacetonitrile (1.25 g.) was added to a solution of L-proline (575 mg.) and triethylamine (0.7 ml.) in a mixture of methanol (7.5 ml.), dioxane (2.5 ml.) and water (5.0 ml.) at room temperature, and the mixture was stirred for 1.5 hours at room temperature. The reaction mixture was concentrated under reduced pressure, and to the residue were added benzene and water. After shaking the resultant mixture, the aqueous layer was separated from the mixture, washed with benzene, acidified with hydrochloric acid, and extracted with ethyl acetate. The extract was washed with water, dried over magnesium sulfate and concentrated. To the residue was added a mixture of ether and n-hexane and the precipitated crystals were collected by filtraton and dried to give N-tert-butoxycarbonyl-L-proline (845 mg.), mp 133° to 134° C.

P. According to a similar manner to that of Example 1 (O), N-tert-butoxycarbonyl-L-leucine hemihydrate (899 mg.), mp 78° to 84° C, was obtained by using L-leucine (656 mg.) and 2-tert-butoxycarbonyloxyimino-2-phenylacetonitrile (1.35 g.) as starting materials.

Q. According to a similar manner to that of Example 1 (O), N-tert-butoxycarbonyl-L-methionine dicyclohexylamine salt (1.768 g.), mp 137° to 139° C, was obtained by using L-methionine (746 mg.) and 2-tert-butoxycarbonyloxyimino-2-phenylacetonitrile (1.35 g.) as starting materials.

R. According to a similar manner to that of Example 1 (O), N-tert-butoxycarbonyl-L-phenylalanine dicyclohexylamine salt (1.463 g.), mp 222° to 223° C (dec.), was obtained by using L-phenylalanine (826 mg.) and 2-tert-butoxycarbonyloxyimino-2-phenylacetonitrile (1.25 g.) as starting materials.

S. According to a similar manner to that of Example 1 (O), N-tert-butoxycarbonyl-L-asparagine (918 mg.), mp 166° to 167° C (dec.), was obtained by using L-asparagine hydrate (0.75 g.) and 2-tert-butoxycarbonyloxyimino-2-phenylacetonitrile (1.85 g.) as starting materials.

T. According to a similar manner to that of Example 1 (O), N-tert-butoxycarbonyl-$N^G$-nitro-L-arginine (2.56 g.), mp 123° to 125° C, was obtained by using $N^G$-nitro-L-arginine (2.20 g.) and 2-tert-butoxycarbonyloxyimino-2-phenylacetonitrile (2.71 g.) as starting materials.

U. According to a similar manner to that of Example 1 (O), N-tert-butoxycarbonyl-L-threonine dicyclohexylamine salt (5.50 g.), mp 152° to 153° C, was obtained by using L-threonine (2.4 g.) and 2-tert-butoxycarbonyloxyimino-2-phenylacetonitrile (5.4 g.) as starting materials.

V. According to a similar manner to that of Example 1 (O), N-tert-butoxycarbonylglycine (1.523 g.), mp 86.5 to 87.5° C, was obtained by using glycine (0.75 g.) and 2-tert-butoxycarbonyloxyimino-2-phenylacetonitrile (2.71 g.) as starting materials.

W. In the similar manner as described in the foregoing Examples 1 (A) to 1 (V), the process for the protection of amino and/or imino group(s) is carried out by using the following various carbonic acid esters, which give the similar results.

1. 2-Ethoxycarbonyloxyimino-2-cyanoacetamide, mp 194° to 196° C.
2. Diethyl 2-ethoxycarbonyloxyiminomalonate, oil.
3. Ethyl 2-ethoxycarbonyloxyimino-2-cyanoacetate, oil.
4. 2-Isobutoxycarbonyloxyimino-2-cyanoacetamide, mp 156° to 158° C.
5. Ethyl 2-isobutoxycarbonyloxyimino-2-cyanoacetate, mp 60° to 62° C.
6. 2-Methoxycarbonyloxyimino-2-cyanoacetamide, mp 174° to 175° C (dec.).
7. Ethyl 2-methoxycarbonyloxyimino-2-cyanoacetate, mp 69° to 71° C.
8. Ethyl 2-(2,2,2-trichloroethoxycarbonyloxyimino)-2-cyanoacetate, mp 51° to 53° C.
9. Ethyl 2-tert-pentyloxycarbonyloxyimino-2-cyanoacetate, oil.
   Infrared Absorption Spectrum
   1810, 1740 cm$^{-1}$
10. 1-Ethoxycarbonyloxy-6-chloro-1H-benzotriazole, mp 160° to 162° C.
11. 1-Benzyloxycarbonyloxy-1H-benzotriazole, mp 130° to 131° C.
12. Benzophenone O-tert-butoxycarbonyloxime, mp 131° to 133° C.
13. 2-tert-Butoxycarbonyloxyimino-2-(4-chlorophenyl)acetonitrile, mp 91° to 92° C.
14. 2-Benzyloxycarbonyloxyimino-2-phenylacetonitrile, mp 73° to 75° C.
15. 2-tert-Butoxycarbonyloxyimino-2-(1-naphthyl)acetonitrile, mp 90° to 92° C.
16. 2-(1-Cyclopropylethoxycarbonyloxyimino)-2-phenylacetonitrile, mp 65° to 67° C.
17. 2-(2,2,2-Trichloroethoxycarbonyloxyimino)-2-phenylacetonitrile, mp 82° to 84° C.

EXAMPLE 2

Preparation of carbonic acid esters

A. Benzene (20 ml.) was added to a solution of phosgene 2.5 g.) in benzene (11.4 ml.). To the solution was dropwise added a solution of diethyl 2-hydroxyiminomalonate (4.73 g.) and N,N-dimethylaniline (3.03 g.) in benzene (30 ml.) over 40 minutes at 5° C in nitrogen stream. The mixture was stirred for 1 hour at the same temperature and overnight at room temperature. To the resultant mixture containing diethyl 2-chlorocarbonyloxyiminomalonate was dropwise added a solution of 4-methoxybenzyl alcohol (3.11 g.) and pyridine (4.04 ml.) in benzene (30 ml.) over 40 minutes at 5° C. The mixture was stirred for 2 hours at the same temperature, for 3 hours at room temperature and allowed to stand overnight. Cold water (100 ml.) was added to the reaction mixture to dissolve an insoluble material and cooled 1N-hydrochloric acid (20 ml.) was added thereto, after which the mixture was shaken. The organic layer was in turn washed 3 times with 1N hydrochloric acid (20 ml.), 3 times with a 5% sodium carbonate aqueous solution (20 ml.) and a sodium chloride aqueous solution, and then dried over magnesium sulfate. After drying the solvent was distilled off to give diethyl 2-(4-methoxybenzyloxycarbonyloxyimino)malonate (6.89 g.), pale brown oil, which was solidified on standing at ambient temperature.

Nuclear Magnetic Resonance Spectrum (CCl$_4$, δ); ppm 6.88, 7.38 (4H, ABq, J=9.0 Hz); 5.23 (2H, s); 4.39 (4H, q, J=7.1 Hz); 3.80 (3H, s); 1.37 (3H, t, J=7.1 Hz); 1.33 (3H, t, J=7.1 Hz).

B. A solution of ethyl 2-hydroxyiminoacetoacetate (3.98 g.) and pyridine (1.98 g.) in benzene (25 ml.) was dropwise added to a solution of phosgene (2.48 g.) in benzene (30 ml.) over 30 minutes at 4° to 5° C. After stirring for 1 hour at the same temperature, the mixture was stirred for 1 hour at room temperature and allowed to stand overnight. To the resultant solution containing ethyl 2-chlorocarbonyloxyiminoacetoacetate was dropwise added, over 30 minutes at 5° to 7° C, a solution of tert-butyl alcohol (3.7 g.) and pyridine (3.96 g.) in benzene (25 ml.). After stirring for 1 hour at the same temperature, the reaction temperature was slowly elevated to room temperature, after which the mixture was stirred for 6 hours at the same temperature and allowed to stand overnight. A precipitate was dissolved by adding about same volume of water to that of the organic layer to the reaction mixture, after which the aqueous layer was separated. The organic layer was in turn washed with a 0.5M citric acid aqueous solution, a 5% sodium carbonate aqueous solution and a sodium chloride aqueous solution, and dried over magnesium sulfate. After drying the solvent was distilled off to give ethyl 2-tert-butoxycarbonyloxyiminoacetoacetate (3.7 g.), oil.

Infrared Absorption Spectrum (Film)
1780, 1730, 1690 cm$^{-1}$

Nuclear Magnetic Resonance Spectrum (CCl$_4$, δ); ppm 4.34 (3H, q); 2.48 (3H, s); 1.57 (9H, s); 1.37 (3H, t).

C. A solution of 2-hydroxyimino-1-phenylbutane-1,3-dione (3.82 g.) and pyridine (1.62 ml.) in benzene (30 ml.) was dropwise added to a solution of phosgene (1.98 g.) in benzene (25 ml.) over 40 minutes at 5° to 9° C. After stirring for 1 hour at the same temperature, the mixture was allowed to stand overnight. To the resultant solution containing 2-chlorocarbonyloxyimino-1-phenylbutane-1,3-dione was dropwise added, over 30 minutes at 5° C, a solution of tert-butyl alcohol (2.96 g.) and pyridine (3.16 g.) in benzene (30 ml.). After stirring for 1 hour at the same temperature, the mixture was stirred for 6 hours at room temperature, after which the mixture was allowed to stand overnight. Cooled water (100 ml.) was added to the reaction mixture, and the organic layer was in turn washed with water, a 0.5M citric acid aqueous solution (20 ml.) (4 times) and a 5% sodium carbonate aqueous solution (20 ml.) (4 times) until the aqueous layer became almost colorless, and further washed with a sodium chloride aqueous solution and then dried over magnesium sulfate. After drying, the solution was treated with activated charcoal and the solvent was distilled off to give oil (3.48 g.). The oil was partly crystallized by allowing to stand and to the mixture was added ether to precipitate crystals. The precipitates were collected by filtration and recrystallized from a mixed solvent of carbon tetrachloride and petroleum ether to give 2-tert-butoxycarbonyloxyimino-1-phenylbutane-1,3-dione (350 mg.), mp 90° to 103° C (dec).

Infrared Absorption Spectrum (Nujol)
1785, 1700, 1680 cm$^{-1}$

Analysis: C$_{15}$H$_{17}$NO$_5$. Calcd.: C 61.85, H 5.88, N 4.81. Found: C 62.99, H 5.92, N 4.98.

D. A solution of phosgene (5 g.) in benzene (23.5 ml.) was dropwise added under ice-cooling to a suspension of 1-hydroxy-6-chloro-1H-benzotriazole (8.5 g.) and pyridine (3.9 g.) in benzene (50 ml.), and the mixture was stirred for 30 minutes at the same temperature and allowed to stand overnight. To the resultant solution containing 1-chlorocarbonyloxy-6-chloro-1H-benzotriazole was dropwise added, over 20 minutes under ice-cooling, a solution of tert-butyl alcohol (3.7 g.) and pyridine (4.0 g.) in benzene (50 ml.). The resultant mixture was stirred for 2 hours at the same temperature and allowed to stand overnight. The reaction mixture was filtered, and the filtrate was concentrated. Ether and petroleum ether were added to the residue to pulverize the residue and obtained crystals were collected by filtration to give 1-tert-butoxycarbonyloxy-6-chloro-1H-benzotriazole (5.3 g.). The mother liquor was concentrated to give the same object compound (0.6 g.). Both crystals were put together and dissolved in benzene, after which the solution was washed with a sodium bicarbonate aqueous solution and water and then dried. The solvent was removed by distillation to give the object compound (3.2 g.), powder, mp 98° to 100° C (dec.).

Analysis: C$_{11}$H$_{12}$N$_3$O$_3$Cl. Calcd.: C 48.98, H 4.48, N 15.58, Cl 13.14. Found: C 49.25, H 4.32, N 15.88, Cl 13.36.

E. A solution of 2-hydroxyimino-2-phenylacetonitrile (7.3 g.) and dimethylaniline (6.0 g) in a mixture of benzene (50 ml) and dioxane (5 ml.) was dropwise added to a solution of phosgene (5.5 g.) in benzene (50 ml.) over 1 hour at 3° to 5° C, and the mixture was stirred for 3.5 hours at the same temperature and allowed to stand overnight. To the resultant solution containing 2-chlorocarbonyloxyimino-2-phenylacetonitrile was dropwise added, over 1 hour under ice-cooling, a solution of tert-butyl alcohol (7.4 g.) and pyridine (5.0 ml.) in benzene (20 ml.). The resultant mixture was stirred for 4 hours at the same temperature, and pyridine (3.0 ml.) was dropwise added thereto, after which the mixture was stirred for 1 hour at room temperature and allowed to stand overnight. Water was added thereto and the organic layer was separated. The organic layer was in turn washed with 1N hydrochloric acid (3 times), a sodium chloride aqueous solution, a sodium bicarbonate aqueous solution (twice) and a sodium chloride aqueous solution (twice) and concentrated. The residue was allowed to stand to give crystals. The crystals were triturated in aqueous methanol, collected by filtration, washed with n-hexane and dried to give 2-tert-butoxycarbonyloxyimino-2-phenylacetonitrile (7.0 g.), mp 84° to 86° C.

Infrared Absorption Spectrum (Nujol)

1785 cm$^{-1}$
Nuclear Magnetic Resonance Spectrum (CDCl$_3$, δ); ppm 7.3 - 8.1 (5H, m); 1.60 (9H, s).
Analysis: C$_{13}$H$_{14}$O$_3$N$_2$. Calcd.: C 63.40, H 5.73, N 11.38. Found: C 63.69, H 5.71, N 11.20.

F. A solution of 2-hydroxyimino-2-phenylacetonitrile (7.3 g), dimethylaniline (6.0 g.) and tert-butyl alcohol (3.7 g.) in benzene (50 ml.) was dropwise added to a solution of phosgene (5.0 g.) in benzene (50 ml.) over 30 minutes under ice-cooling. To the mixture was dropwise added a solution of pyridine (4.0 ml.) in benzene (20 ml.) and the mixture was stirred for 1 hour at the same temperature and allowed to stand overnight. Water and benzene were added to the reaction mixture and an insoluble material was filtered off. The organic layer was in turn washed with 1N hydrochloric acid, water, a sodium bicarbonate aqueous solution and water, and dried over magnesium sulfate. The solvent was distilled off and to the residue were added n-hexane and a small amount of methanol. An insoluble material was filtered off and the filtrate was concentrated. Methanol was added to the residue and the mixture was allowed to stand. The precipitates were collected by filtration to give 2-tert-butoxycarbonyloxyimino-2-phenylacetonitrile (3.5 g.). Mp 83° to 85° C. Water was added to the mother liquor and the mixture was allowed to stand. The precipitates were collected by filtration to give the object compound (1.5 g.). Total yield (5.0 g.).

G. A solution of 2-hydroxyimino-2-phenylacetonitrile (14.6 g.) and dimethylaniline (13.2 g.) in a mixture of acetone (5 ml.) and benzene (80 ml.) was dropwise added to a solution of trichloromethyl chloroformate (phosgene dimer) (6.7 ml.) in benzene (30 ml.) under ice-cooling. The mixture was stirred for 6 hours at the same temperature and allowed to stand overnight. To the resultant mixture containing 2-chlorocarbonyloxyimino-2-phenylacetonitrile was dropwise added a mixture of tert-butyl alcohol (11.1 g.), pyridine (16.0 ml.) and benzene (20 ml.) under ice-cooling, and the mixture was stirred for 7 hours at room temperature and allowed to stand overnight. The reaction mixture was treated as described in the above Examples 2(A) to 2(F) to give 2-tert-butoxycarbonyloxyimino-2-phenylacetonitrile (17.0 g.), mp 84° to 86° C.

H. A solution of dimethylaniline (6.0 ml.) in benzene (15 ml.) was dropwise added to a suspension of 2-hydroxyimino-2-phenylacetonitrile (7.3 g.) and phosgene (5.0 g.) in benzene (50 ml.) over 40 minutes under ice-cooling. The mixture was stirred for 2 hours at the same temperature and allowed to stand overnight. To the mixture containing 2-chlorocarbonyloxyimino-2-phenylacetonitrile was dropwise added a solution of 4-methoxybenzyl alcohol (6.9 g.) and pyridine (4.0 ml.) in benzene (20 ml.) over 30 minutes under ice-cooling, and the mixture was stirred for 7 hours at room temperature. The reaction mixture was in turn washed with water, 1N hydrochloric acid, water, a sodium bicarbonate aqueous solution and water, and dried over magnesium sulfate. The solution was concentrated, and the residual crystals were triturated in n-hexane and collected by filtration. The crystals were recrystallized from a mixture of ethyl acetate and n-hexane to give 2-(4-methoxybenzyl)oxycarbonyloxyimino-2-phenylacetonitrile (3.1 g.). Mp 112° to 113° C. The mother liquor was concentrated to give the object compound (2.4 g.). Total yield (5.5 g.).

Infrared Absorption Spectrum (Nujol)
1785 cm$^{-1}$
Nuclear Magnetic Resonance Spectrum (CDCl$_3$, δ); ppm 6.8 - 8.0 (9H, m); 5.30 (2H, s); 3.80 (3H, s).
Analysis: C$_{17}$H$_{14}$O$_4$N$_2$. Calcd.: C 65.79, H 4.54, N 9.03. Found: C 65.99, H 4.38, N 9.03.

I. A solution of 2-hydroxyimino-2-phenylacetonitrile (14.6 g) and dimethylaniline (13.2 g.) in a mixture of benzene (80 ml.) and dioxane (8 ml.) was dropwise added to a solution of trichloromethyl chloroformate (phosgene dimer) (11 g.) in benzene (50 ml.) under ice-cooling, and the mixture was stirred for 3 hours at the same temperature and allowed to stand overnight. To the mixture containing 2-chlorocarbonyloxyimino-2-phenylacetonitrile was dropwise added a solution of tert-butyl alcohol (14.8 g.) and pyridine (16.0 ml.) in benzene (20 ml.) under ice-cooling. The reaction mixture was stirred for 6 hours together with gradual elevation of the reaction temperature to room temperature and allowed to stand overnight. Water was added to the reaction mixture, and the organic layer was separated. The organic layer was in turn washed with 1N hydrochloric acid, a sodium chloride aqueous solution, a sodium bicarbonate aqueous solution and water and then dried. The solvent was distilled off, and methanol was added to the residue. The mixture was cooled by ice-water, and the precipitates were collected by filtration and washed with a small amount of cooled methanol to give 2-tert-butoxycarbonyloxyimino-2-phenylacetonitrile (9.5 g.). From the mother liquor the object compound (9.4 g.) was further obtained. Both of the object compounds obtained above were combined and recrystallized from methanol to give the pure compound (14.6 g.), mp 84° to 86° C.

J. A solution of benzophenone oxime (9.85 g.) and dimethylaniline (6.6 g.) in a mixture of benzene (50 ml.) and dioxane (10 ml.) was dropwise added to a solution of trichloromethyl chloroformate (phosgene dimer) (5.5 g.) in benzene (15 ml.) under ice-cooling, and the mixture was stirred for 1 hour at the same temperature, for 2 hours at room temperature and allowed to stand overnight. To the resultant mixture containing benzophenone O-chlorocarbonyloxime was dropwise added a solution of tert-butyl alcohol (5.6 g.) and pyridine (6.0 ml.) in benzene (20 ml.) under ice-cooling, and the mixture was stirred for 6 hours at the same temperature and allowed to stand overnight. The reaction mixture was in turn washed with water, 1N hydrochloric acid, water, a sodium bicarbonate aqueous solution and water, and dried over magnesium sulfate. The solvent was distilled off and to the resulting crystals was added petroleum ether. The crystals were collected by filtration and dried to give benzophenone O-tert-butoxycarbonyloxime (10.5 g.), mp 126° to 133° C. A small amount of the crystals was recrystallized from a mixture of toluene and petroleum ether to give pure compound, mp 131° to 133° C.
Infrared Absorption Spectrum (Nujol)
1770 cm$^{-1}$
Nuclear Magnetic Resonance Spectrum (CDCl$_3$, δ); ppm 7.17 - 7.65 (10H, m); 1.48 (9H, s).

K. A suspension of 2-hydroxyimino-2-(4-chlorophenyl)acetonitrile (6.75 g.) and dimethylaniline (4.5 g.) in a mixture of dichloromethane (70 ml.), dioxane (10 ml.) and tetrahydrofuran (10 ml.) was dropwise added to a solution of trichloromethyl chloroformate (phosgene dimer) (16 g.) in benzene (22 ml.) under ice-cooling, and the mixture was stirred for 5 hours at the same temperature and allowed to stand overnight. To the resultant mixture containing 2-chlorocarbonyloxyimino-2-(4-chlorophenyl)acetonitrile was dropwise added a solution of tert-butyl alcohol (8.9 g.) and pyridine (9.6 ml.) in dichloromethane (20 ml.) under ice-cooling, and the mixture was stirred for 5 hours at the same temperature and allowed to stand for 48 hours. The reaction mixture was in turn washed with water, 1N hydrochloric acid, water, a sodium bicarbonate aqueous solution and water, and dried over magnesium sulfate. The solvent was distilled off and n-hexane was added to the residue. An insoluble material was filtered off and the filtrate was concentrated. To the residue was added petroleum ether and the mixture was allowed to stand to precipitate crystals. The crystals were dissolved in hot petroleum ether and the solution was filtered. The filtrate was cooled to precipitate crystals and the crystals were collected by filtration to give 2-tert-butoxycarbonyloxyimino-2-(4-chlorophenyl)acetonitrile (1.6 g.). These crystals were recrystallized from methanol to give the pure compound (0.7 g.), mp 91° to 92° C.

Infrared Absorption Spectrum (Nujol)
1790 cm$^{-1}$
Nuclear Magnetic Resonance Spectrum (CDCl$_3$, δ); ppm 7.90 (2H, ABq, J=4.5Hz); 7.50 (2H, ABq, J=4.5Hz); 1.63 (9H, s).

L. (1) Preparation of the starting compound:

2-(1-naphthyl)acetonitrile (16.7 g.) was added to a solution of sodium hydroxide (4.2 g.) in methanol (80 ml.). To the mixture was introduced under ice-cooling gaseous methyl nitrite which was prepared by adding a solution of conc sulfuric acid (5 ml.) in water (10 ml.) to a solution of sodium nitrite (8.3 g.) in a mixture of methanol (5.5 ml.) and water (5 ml.). The mixture was stirred for 4 hours at the same temperature and the reaction mixture was treated by conventional method to give 2-hydroxyimino-2-(1-naphthyl)acetonitrile (7.1 g.), oil.

Infrared Absorption Spectrum (Film)
1700 cm$^{-1}$

2. Preparation of the object compound:

A solution of 2-hydroxyimino-2-(1-naphthyl)acetonitrile (7.0 g.) and dimethylaniline (12.0 g.) in toluene (100 ml.) was dropwise added under ice-cooling to a solution of trichloromethyl chloroformate (phosgene dimer) (3.56 g.) in benzene (30 ml.). The mixture was stirred for 3 hours at the same temperature and allowed to stand overnight. To the resultant mixture containing 2-chlorocarbonyloxyimino-2-(1-naphthyl)acetonitrile was dropwise added a solution of tert-butyl alcohol (11.1 g.) and pyridine (12 ml.) in toluene (20 ml.) under ice-cooling, and the mixture was stirred for 6 hours at the same temperature and allowed to stand overnight. The reaction mixture was in turn washed with water, 1N hydrochloric acid, water, a sodium bicarbonate aqueous solution and water, and dried over magnesium sulfate. The solution was concentrated under reduced pressure and to the residue were added n-hexane and methanol. The mixture was allowed to stand in a refrigerator, and the precipitated crystals were collected by filtration and recrystallized twice from methanol to give 2-tert-butoxycarbonyloxyimino-2-(1-naphthyl)acetonitrile (3.3 g.), mp 90° to 92° C.

Analysis: C$_{17}$H$_{16}$O$_3$N$_2$. Calcd.: C 68.90, H 5.44, N 9.46. Found: C 68.85, H 5.38, N 9.40.

Infrared Absorption Spectrum (Nujol)
1790 cm$^{-1}$

M. A solution of 2-hydroxyimino-2-phenylacetonitrile (2.2 g.) and dimethylaniline (1.80 g.) in a mixture of benzene (25 ml.) and dioxane (3 ml.) was dropwise added to a solution of trichloromethyl chloroformate (phosgene dimer) (1.5 g.) in benzene (20 ml.) under ice-cooling. The mixture was stirred for 3 hours at the same temperature and allowed to stand overnight. To the resultant mixture containing 2-chlorocarbonyloxyimino-2-phenylacetonitrile was dropwise added a solution of 1-cyclopropylethanol (1.4 g.) and pyridine (1.2 ml.) in benzene (10 ml.) under ice-cooling. The mixture was stirred for 2 hours at the same temperature, for 4 hours at room temperature and allowed to stand overnight. The reaction mixture was in turn washed with 1N hydrochloric acid, water, a sodium bicarbonate aqueous solution and water, and dried over magnesium sulfate. The solvent was distilled off and to the oily residue was added a small amount of methanol. The mixture was allowed to stand in a refrigerator, and the precipitated crystals were collected by filtration and recrystallized from methanol to give 2-(1-cyclopropylethoxycarbonyloxyimino)-2-phenylacetonitrile (0.7 g.), mp 65° to 67° C.

Infrared Absorption Spectrum (Nujol)
1785 cm$^{-1}$

Analysis: C$_{14}$H$_{14}$O$_3$N$_2$. Calcd.: C 65.10, H 5.46, N 10.85. Found: C 65.07, H 5.15, N 10.84.

N. The following compounds were obtained according to a similar manner to those of Examples 2(A) to 2(M).

1. 1-Ethoxycarbonyloxy-6-chloro-1H-benzotriazole, mp 160° to 162° C.
2. 1-Benzyloxycarbonyloxy-1H-benzotriazole, mp 130° to 131° C.
3. 2-Benzyloxycarbonyloxyimino-2-phenylacetonitrile, mp 73° to 75° C.
4. 2-(2,2,2-Trichloroethoxycarbonyloxyimino)-2-phenylacetonitrile, mp 82° to 84° C.

EXAMPLE 3

Preparation of carbonic acid esters

A. Ether (10 ml.) was added to a solution of phosgene (2 g.) in benzene (12.4 ml.). To the solution was dropwise added a solution of 4-methoxybenzyl alcohol (2.76 g.) in ether (10 ml.) over 25 minutes at −10° C with stirring and paying attention to exotherm. The mixture was stirred for 20 minutes at −10° to −7° C and phosgene was removed by introducing nitrogen stream for 15 minutes at the same temperature. To the resultant solution containing 4-methoxybenzyl chloroformate was added a solution of diethyl 2-hydroxyiminomalonate (3.78 g.) in benzene (20 ml.) over 10 minutes and then was added a solution of triethylamine (5.6 ml.) in benzene (20 ml.) over 30 minutes at −7° to −2° C. Benzene (20 ml.) was added thereto and the mixture was stirred for 30 minutes at 5° C, for 1 hour at room temperature and allowed to stand for 64 hours. Water was added to the reaction mixture to dissolve an insoluble material and the organic layer was in turn washed with water, 3 times with a 0.5M citric acid aqueous solution (20 ml.), 3 times with a 5% sodium carbonate aqueous solution (20 ml.) and a sodium chloride aqueous solution, and then dried over magnesium sulfate. After drying the solvent was distilled off to give diethyl 2-(4-methoxybenzyloxycarbonyloxyimino)malonate (5.62 g.), oil.

B. A solution of ethyl chloroformate (2.17 g.) in benzene (10 ml.) was dropwise added to a solution of 1-hydroxy-6-chloro-1H-benzotriazole (3.38 g.) and triethylamine (2.80 ml.) in benzene (30 ml.) under ice-cooling and stirring. Benzene (30 ml.) was further added to the mixture and the reaction temperature was slowly elevated to room temperature, and the mixture was allowed to stand overnight. Precipitated crystals were filtered off and the filtrate was concentrated. Benzene was added to the residue and an insoluble material was filtered off, after which the filtrate was concentrated to give 1-ethoxycarbonyloxy-6-chloro-1H-benzotriazole (2.2 g.), crystal. These crystals, the precipitated crystals filtered off and the insoluble material in benzene were put together, in turn washed with water, a sodium bicarbonate aqueous solution, 1N hydrochloric acid and water, and recrystallized from methanol (75 ml.) to give the object compound (3.5 g.), white needles, mp 160° to 162° C.

Analysis: $C_9H_8N_3O_3Cl$. Calcd.: C 44.73, H 3.36, N 17.39, Cl 14.67. Found: C 44.71, H 3.25, N 17.34, Cl 14.72.

C. Benzyl chloroformate (8.5 g.) was dropwise added under ice-cooling to a solution of 1-hydroxy-1H-benzotriazole (6.8 g.) and triethylamine (7.0 ml.) in a mixture of benzene (100 ml.) and water (50 ml.), and the mixture was stirred for 3 hours at the same temperature. The reaction mixture was filtered and the precipitated crystals were washed with water and dried. The benzene layer was washed with water, dried and concentrated. The residue and the crystals above obtained were put together and recrystallized from a mixed solvent of benzene and petroleum ether to give 1-benzyloxycarbonyloxy-1H-benzotriazole (12.1 g.), mp 130° to 131° C.

Analysis: $C_{14}H_{11}N_3O_3$. Calcd.: C 62.44, H 4.12, N 15.61. Found: C 62.62, H 4.16, N 15.49.

D. A solution of benzyl chloroformate (5.1 g.) in ether (40 ml.) was added to a solution of 2-hydroxyimino-2-phenylacetonitrile (4.4 g.) in a mixture of a 1N potassium hydroxide aqueous solution (30 ml.) and dioxane (10 ml.) under ice-cooling, and the mixture was stirred for 1 hour at the same temperature and for 4 hours at room temperature. The ether layer was separated from the reaction mixture and the aqueous layer was further extracted with ether. Both ether layers were combined, washed with water and dried over magnesium sulfate. The solvent was distilled off and to the residue was added n-hexane. The precipitated crystals were collected by filtration to give 2-benzyloxycarbonyloxyimino-2-phenylacetonitrile (5.2 g.), mp 73° to 75° C.

Infrared Absorption Spectrum (Nujol)
1795 cm⁻¹

E. A solution of 2,2,2-trichloroethyl chloroformate (2.2 g.) in benzene (10 ml.) was dropwise added to a solution of 2-hydroxyimino-2-phenylacetonitrile (1.5 g.) and triethylamine (1.40 ml.) in benzene (20 ml.) at room temperature, and the mixture was stirred for 3 hours at the same temperature. To the reaction mixture were added benzene and water, and the organic layer was washed with water and dried over magnesium sulfate. The solvent was distilled off and the residue was crystallized by adding a small amount of ether and n-hexane. The crystals were collected by filtration and recrystallized from methanol to give 2-(2,2,2-trichloroethoxycarbonyloxyimino)-2-phenylacetonitrile (2.7 g.), mp 82° to 84° C.

Infrared Absorption Spectrum (Nujol)
1800, 1790 cm⁻¹

Analysis: $C_{11}H_7O_3N_2Cl_3$. Calcd.: C 41.08, H 2.19, N 8.71, Cl 33.08. Found: C 41.29, H 2.05, N 8.81, Cl 32.31.

F. The following compounds were obtained according to a similar manner to those of Examples 3(A) to 3(E).

1. Ethyl 2-tert-butoxycarbonyloxyiminoacetoacetate, oil.

Infrared Absorption Spectrum (Film)
1780, 1730, 1690 cm⁻¹

2. 2-tert-Butoxycarbonyloxyimino-1-phenylbutane-1,3-dione, mp 90° to 103° C (dec.).

3. 1-tert-Butoxycarbonyloxy-6-chloro-1H-benzotriazole, mp 98° to 100° C (dec.).

4. 2-tert-Butoxycarbonyloxyimino-2-phenylacetonitrile, mp 84° to 86° C.

5. 2-(4-Methoxybenzyloxycarbonyloxyimino)-2-phenylacetonitrile, mp 112° to 113° C.

6. Benzophenone O-tert-butoxycarbonyloxime, mp 131° to 133° C.

7. 2-tert-Butoxycarbonyloxyimino-2-(4-chlorophenyl)acetonitrile, mp 91° to 92° C.

8. 2-tert-Butoxycarbonyloxyimino-2-(1-naphthyl)acetonitrile, mp 90° to 92° C.

9. 2-(1-Cyclopropylethoxycarbonyloxyimino)-2-phenylacetonitrile, mp 65° to 67° C.

What we claim is:

1. Carbonic acid esters of the formula:

wherein R'₁ is lower alkyl which may have substituent(s) selected from the group of halogen, lower alkoxy and aryloxy, or ar(lower)-alkyl which may have substituent(s) selected from the group of lower alkoxy, halogen, nitro and cyano, and R'₂ is benzotriazolyl which may have halogen as a substituent; or a group represented by the formula:

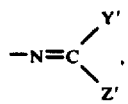

wherein Y' and Z' are each cyano, nitro, carbamoyl, esterified carboxy, lower alkanoyl, aroyl or disubstituted carbamoyl; provided that when R'₂ is a group represented by the formula:

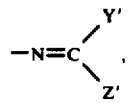

wherein Y' and Z' are each cyano, nitro, carbamoyl or esterified carboxy,

R'₁ is ar(lower)alkyl having substituent(s) selected from the group of lower alkoxy, halogen, nitro and cyano.

2. The compounds according to claim 1, wherein R'₂ is a group represented by the formula:

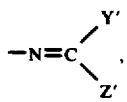

wherein Y' and Z' are each cyano, nitro, carbamoyl, esterified carboxy, lower alkanoyl, aroyl or disubstituted carbamoyl.

3. The compounds according to claim 2, wherein $R'_1$ is lower alkyl, or ar(lower)alkyl having lower alkoxy, and $R'_2$ is a group represented by the formula:

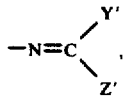

wherein Y' is esterified carboxy or aroyl and Z' is esterified carboxy or lower alkanoyl; provided that when Y' and Z' are both esterified carboxy, $R'_1$ is ar(lower)alkyl having lower alkoxy.

4. The compounds according to claim 3, wherein $R'_1$ is lower alkyl, Y' is esterified carboxy or aroyl and Z' is lower alkanoyl.

5. The compounds according to claim 4, wherein Y' is lower alkoxycarbonyl or aroyl.

6. The compounds according to claim 5, wherein $R'_1$ is tert-butyl, Y' is ethoxycarbonyl, or benzoyl and Z' is acetyl.

7. The compound according to claim 6, wherein Y' is ethoxycarbonyl.

8. The compound according to claim 6, wherein Y' is benzoyl.

9. The compounds according to claim 3, wherein $R'_1$ is ar(lower)alkyl having lower alkoxy, and Y' and Z' are both esterified carboxy.

10. The compounds according to claim 9, wherein Y' and Z' are both lower alkoxycarbonyl.

11. The compounds according to claim 10, wherein $R'_1$ is benzyl having methoxy, and Y' and Z' are both ethoxycarbonyl.

12. The compound according to claim 11, wherein $R'_1$ is 4-methoxybenzyl.

13. The compounds according to claim 1, wherein $R'_1$ is lower alkyl or ar(lower)alkyl and $R'_2$ is benzotriazolyl which may have halogen as a substituent.

14. The compounds according to claim 13, wherein $R'_1$ is ethyl, tert-butyl or benzyl and $R'_2$ is benzotriazolyl which may have chlorine as a substituent.

15. The compounds according to claim 14, wherein $R'_2$ is 1H-benzotriazol-1-yl or 6-chloro-1H-benzotriazol-1-yl.

16. The compound according to claim 15, wherein $R'_1$ is ethyl and $R'_2$ is 6-chloro-1H-benzotriazol-1-yl.

17. The compound according to claim 15, wherein $R'_1$ is tert-butyl and $R'_2$ is 6-chloro-1H-benzotriazol-1-yl.

18. The compound according to claim 15, wherein $R'_1$ is benzyl and $R'_2$ is 1H-benzotriazol-1-yl.

19. A process for preparing carbonic acid esters of the formula:

$$R'_1OCOOR'_2$$

wherein $R'_1$ is lower alkyl which may have substituent(s) selected from the group of halogen, lower alkoxy and aryloxy, or ar(lower)-alkyl which may have substituent(s) selected from the group of lower alkoxy, halogen, nitro and cyano, and $R'_2$ is benzotriazolyl which may have halogen as a substituent; or a group represented by the formula:

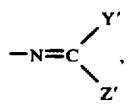

wherein Y' and Z' are each cyano, nitro, carbamoyl, esterified carboxy, lower alkanoyl, aroyl or disubstituted carbamoyl; provided that when $R'_2$ is a group represented by the formula:

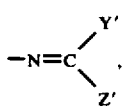

wherein Y' and Z' are each cyano, nitro, carbamoyl or esterified carboxy, $R'_1$ is ar(lower)alkyl having substituent(s) selected from the group of lower alkoxy, halogen, nitro and cyano; which comprises a. reacting a haloformic acid ester of the formula:

$$X—COOR'_1$$

wherein X is halogen and $R'_2$ is as defined above, with a hydroxy-compound of the formula:

$$R'_1 — OH$$

wherein $R'_1$ is as defined above, or b. reacting a formic acid ester of the formula:

$$R'_1—OCOX'$$

wherein $R'_1$ is as defined above and X' is halogen, with a compound of the formula:

$$R'_2 — OH$$

wherein $R'_2$ is as defined above or a salt thereof.

20. Compounds according to claim 1 wherein $R'_1$ is lower alkyl and $R'_2$ is benzotriazolyl which may have halogen as a substituent.

21. Compounds according to claim 20 wherein $R'_1$ is ethyl or tertiary butyl and $R'_2$ is benzotriazolyl which may have chlorine as a substituent.

22. Compounds according to claim 21 wherein $R'_2$ is 1H-benzotriazol-1-yl or 6-chloro-1H-benzotriazol-1-yl.

* * * * *